US012681012B2

(12) United States Patent
Kaczmarski et al.

(10) Patent No.: US 12,681,012 B2
(45) Date of Patent: Jul. 14, 2026

(54) BIOSENSOR AND A BIOSENSING KIT

(71) Applicant: IQ BIOZOOM SP. Z O.O., Stalowa Wola (PL)

(72) Inventors: Jakub Kaczmarski, Warsaw (PL); Dorota Dardzinska, Warsaw (PL); Katarzyna Kaczmarska, Warsaw (PL)

(73) Assignee: IQ BIOZOOM SP. Z O. O., Stalowa Wola (PL)

( * ) Notice: Subject to any disclaimer, the term of this patent is extended or adjusted under 35 U.S.C. 154(b) by 368 days.

(21) Appl. No.: 18/241,871

(22) Filed: Sep. 3, 2023

(65) Prior Publication Data

US 2024/0077476 A1    Mar. 7, 2024

(30) Foreign Application Priority Data

Sep. 2, 2022    (EP) ..................................... 22461602

(51) Int. Cl.
| | |
|---|---|
| *G01N 33/543* | (2006.01) |
| *G01N 27/327* | (2006.01) |
| *G01N 27/414* | (2006.01) |

(52) U.S. Cl.
CPC ... G01N 33/54373 (2013.01); G01N 27/3275 (2013.01); G01N 27/4143 (2013.01)

(58) Field of Classification Search
CPC ......... G01N 33/54373; G01N 27/3275; G01N 27/4143
See application file for complete search history.

(56) References Cited

U.S. PATENT DOCUMENTS

| | | |
|---|---|---|
| 2010/0194409 A1 | 8/2010 | Gao et al. |
| 2011/0132773 A1 | 6/2011 | Liemersdorf et al. |
| 2014/0264467 A1* | 9/2014 | Cheng ................ G01N 27/4148 257/253 |
| 2015/0276667 A1 | 10/2015 | Klootwijk et al. |

(Continued)

OTHER PUBLICATIONS

Jeseung Oh et al. "A carbon nanotube metal semiconductor field effect transistor-based biosensor for detection of amyloid-beta in human serum", Biosensors and Bioelectronics, vol. 50, 2013, pp. 345-350, ISSN 0956-5663, https://doi.org/10.1016/j.bios.2013.07.004.

(Continued)

*Primary Examiner* — Christine A Enad
(74) *Attorney, Agent, or Firm* — Rivka Friedman

(57) ABSTRACT

A biosensor with a detection transistor of a metal-semiconductor field-effect (MESFET) type, for detecting a target substance. The detection transistor has an isolating substrate, a source electrode, a drain electrode, a first gate electrode, a channel for transmitting a drain-source current between the source electrode and the drain electrode, the channel being made of an oxide semiconductor, arranged on the isolating substrate and having the source electrode and the drain electrode arranged thereon, a sensitive substrate connected to the first gate electrode and including functionalization species for bonding the target substance, such that the first gate electrode connected with said substrate is sensitive to the target substance, and a second gate electrode arranged on the isolating substrate, physically separated from the first gate electrode by the channel, positioned opposite to the first gate electrode and aimed to modulate the drain-source current of the channel.

14 Claims, 6 Drawing Sheets

(56) References Cited

U.S. PATENT DOCUMENTS

| | | | |
|---|---|---|---|
| 2015/0330941 A1* | 11/2015 | Smith | ............... G01N 27/4148 |
| | | | 257/253 |
| 2016/0202208 A1 | 7/2016 | Lee et al. | |
| 2021/0003528 A1* | 1/2021 | Esquivel-Upshaw | ........................ |
| | | | G01N 27/4146 |

OTHER PUBLICATIONS

Jakub Kaczmarski, "IGZO MESFET with enzyme-modified Schottky gate electrode for glucose sensing" Japanese Journal of Applied Physics, vol. 58, No. 9. DOI 10.7567/1347-4065/ab1a65.

* cited by examiner

BIOSENSOR AND A BIOSENSING KIT

TECHNICAL FIELD

The present invention relates to a biosensor comprising a metal-semiconductor field-effect transistor, and to a biosensing kit suitable for detecting various target substances in a liquid sample, including but not Limited to biological substances such as proteins, sugars, antigens, and nucleic acid sequences, etc.

BACKGROUND

Field-effect transistors (FETs), including metal-semiconductor field-effect transistors (MESFETs), serve as biosensor components for detecting target substances in liquid samples, including samples of biological liquids such as saliva, urine, sweat, or blood. Typical detection methods using these biosensors involve exposing a sensitive area of the transistor to the liquid sample. This sensitive area usually comprises functionalization species that can interact with the target substance within the liquid sample. During the detection process, this interaction affects the source-drain current in the transistor channel, allowing the presence and/or concentration of the target substance in the sample to be determined.

However, known designs of biosensors based on FET-type transistors often encounter issues related to the influence of external factors during the assay. Specifically, the temperature or pH of samples and other so-called external interfering factors may distort the measurement results, leading to unreliable data.

SUMMARY OF THE INVENTION

The present invention aims to provide an alternative apparatus for detecting substances, capable of detecting a target substance, wherein at least some of the interfering factors can be compensated, thereby improving the signal-to-noise ratio for the obtained results.

In one aspect, the invention pertains to a biosensor comprising a detection transistor of a metal-semiconductor field-effect (MESFET) type, for detecting a target substance. The detection transistor comprises: a source electrode, a drain electrode, a first gate electrode, and a channel for transmitting a drain-source current ($I_{DS}$) between the source electrode and the drain electrode. The channel is made of an oxide semiconductor. The source electrode and the drain electrode are arranged on the channel that is arranged on an isolating substrate; and the detection transistor further comprises: a sensitive substrate connected to the first gate electrode and comprising functionalization species for bonding the target substance, such that the first gate electrode connected with said substrate is sensitive to the target substance and a second gate electrode arranged on the isolating substrate, physically separated from the first gate electrode by the channel, positioned opposite to the first gate electrode and configured to modulate the drain-source current ($I_{DS}$) of the channel.

This arrangement of the second gate electrode allows for modulation of the drain-source current, which in turn enables adequate compensation for the influence of external factors, including the presence of electrolytes or nitrogenous species in the sample (which could interfere with the obtained results). The biosensor comprising said detection transistor exhibits improved stabilization of its operation point, resulting in increased reliability of the assay outcome.

This is achieved by controlling the transconductance of the channel layer of the TFT using a microcontroller. As a result, changes in the $I_{DS}$ of the biosensing transistors correspond to changes in the concentration of monitored species in the analyte. Various types of isolating substrates can be used, such as plastics (for example, polyethylene terephthalate (PET), polyethylene naphthalate (PEN)) or glass. This substrate allows the biosensing transistor to be formed using a variety of known physical and chemical techniques. The use of the oxide semiconductor to form the channel allows the transistor to be fabricated on substrates sensitive to high temperatures, such as plastics. Furthermore, the biosensing transistor having the channel made of an oxide semiconductor is more stable over time than if another material was used for the channel, such as organic semiconductors or carbon nanotubes.

The second gate electrode provides additional stabilization for the operating point of the detection transistor. The isolating substrate protects the transistor from external conditions. Preferably, the substrate is elastic, such as a PET foil, a PEN foil, or a Kapton foil, which facilitates the production of the biosensor as part of a wearable device, such as one worn on the wrist.

The placement of the second gate electrode on the isolating substrate protects the second gate electrode from external conditions while allowing it to modulate the drain-source current in the channel. The second gate electrode can be positioned along the channel in an area to which at the opposite side of the channel there is adjacent the first gate electrode and optionally only one of the source electrode or the drain electrode. By limiting the area of the second gate electrode, the operating point of the transistor can be precisely controlled, limiting the leakage currents of the second gate and increasing the stability of the transistor's operation.

The biosensor may also include an encapsulation arranged to expose the first gate electrode. This encapsulation provides further protection for the transistor from environmental factors such as moisture or oxygen, while allowing for the connection of the first gate electrode with the sensitive substrate.

The first gate electrode can be connected with the sensitive substrate via a deposition of the substrate on the first gate electrode. This direct deposition makes the biosensor more compact, easier to store, and simpler to handle. Furthermore, this deposition can be completed during the manufacturing of the transistor, making the transistor ready-to-use upon purchase, therefore the users do not have to attach the sensitive substrate by themselves. This is particularly convenient for inexperienced or occasional users.

The first gate electrode can be connected with the sensitive substrate via a conductive path, preferably selected from a group consisting of conductive film, wiring, junction connector, and electrolytic connection. The sensitive substrate can be designed to be detachably attached to the first gate electrode, allowing the transistor to be reused and the sensitive substrate to be replaced after each use. This is particularly convenient for experienced or frequent users, such as those who use the device on a regular basis, e.g. daily for glucose monitoring.

The sensitive substrate can be arranged on a disposable strip comprising a sheet of material with functionalization species for detachable connection with the first gate electrode. This design makes the sensitive substrate disposed on a disposable strip is less prone to damage and easier to handle and combine with the first gate electrode of the detection transistor.

The biosensor may further comprise a reference transistor of a metal-semiconductor field-effect (MESFET) type, the reference transistor comprising: a source electrode, a drain electrode, a first gate electrode connected with an insensitive substrate without the functionalization species of the sensitive substrate, such that the first electrode connected with said insensitive substrate is insensitive to the target substance, a channel made of the oxide semiconductor, for transmitting a drain-source current between the source electrode and the drain electrode, and a second gate electrode physically separated from the first gate electrode by the channel. The detection transistor and the reference transistor can be both placed on the isolating substrate and electrically connected to one another by the second gate electrodes. The reference transistor provides further stabilization of the operating point of the biosensor. The reference transistor can be configured to measure the various external factors such as pH of the sample thereby providing more accurate assay results. Further, the arrangement of the second gate electrodes of the detection and reference sensors as described above provides increase in the measurement stability, by selecting the operation point and thus increase in the measurement accuracy, sensitivity and specificity of the device.

The second gate electrode of the detection transistor and the second gate electrode of the reference transistor can be arranged as a common second gate electrode of both transistors, formed from a single piece of material. This design simplifies production, reduces costs, and lowers the failure rate, since both second gate electrodes can be produced in one step.

The detection transistor and the reference transistor can be covered with a common encapsulation, thereby further simplifying the manufacturing process of the biosensor, as providing the substrate and encapsulating can be accomplished faster. The common second gate electrode may extend from the channel of the detection transistor to the channel of the reference transistor, wherein said channels separate the common second gate electrode from the first gate electrodes of both transistors. Such design provides adequate modulation of the drain-source current of both, the detection transistor and the reference transistor.

In another aspect, the present invention relates to a biosensing device comprising the biosensor as described herein and further comprising: a control unit for processing measured data, a power supply unit for powering the device, and a data display unit for visualizing detection results.

In yet another aspect, the present invention relates to a biosensing kit comprising the biosensor as described herein and a disposable substrate unit comprising a sensitive substrate with functionalization species sensitive to the target substance, which can be detachably connected with the first gate electrode of the detection transistor.

In a further aspect, the present invention relates to a biosensing kit comprising the biosensor as described herein and a disposable substrate unit comprising a sensitive substrate with functionalization species sensitive to the target substance, which can be detachably connected with the first gate electrode of the detection transistor, and an insensitive substrate without functionalization species sensitive to the target substance, which can be detachably connected with the first gate electrode of the reference transistor. This kit allows for multiple uses of the biosensing unit, with the used strip being replaced with a new one for each new assay to be carried out.

Further aspects and features of the present invention are described in the following description of the drawings.

BRIEF DESCRIPTION OF DRAWINGS

Aspects and features of the present invention will become apparent by describing, in detail, exemplary embodiments of the present invention with reference to the attached drawings, showing.

DETAILED DESCRIPTION OF EMBODIMENTS

Figure 1A:
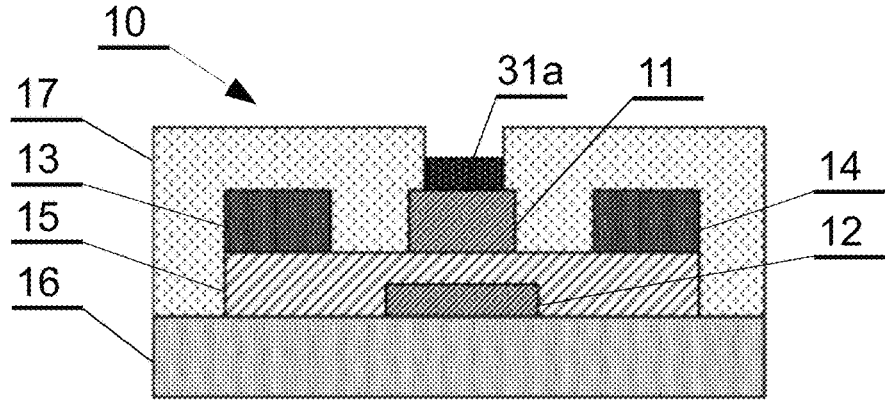
FIG. 1A: a cross-sectional view of a first embodiment of a detection transistor.

Reference will now be made to embodiments, examples of which are illustrated in the accompanying drawings. Aspects and features of the embodiments will be described with reference to the accompanying drawings. In the drawings, like reference numerals denote like elements. The present invention, however, may be embodied in various different forms and should not be construed as being limited only to the illustrated embodiments. Rather, these embodiments are provided as examples so that this disclosure will be thorough and complete, and will fully convey the aspects and features of the present invention to those skilled in the art. It shall be understood that not all of the features shown in the embodiments are essential and the scope of the protection is defined not by means of literally shown embodiments, but by the features provided in the claims.

Figure 1B:
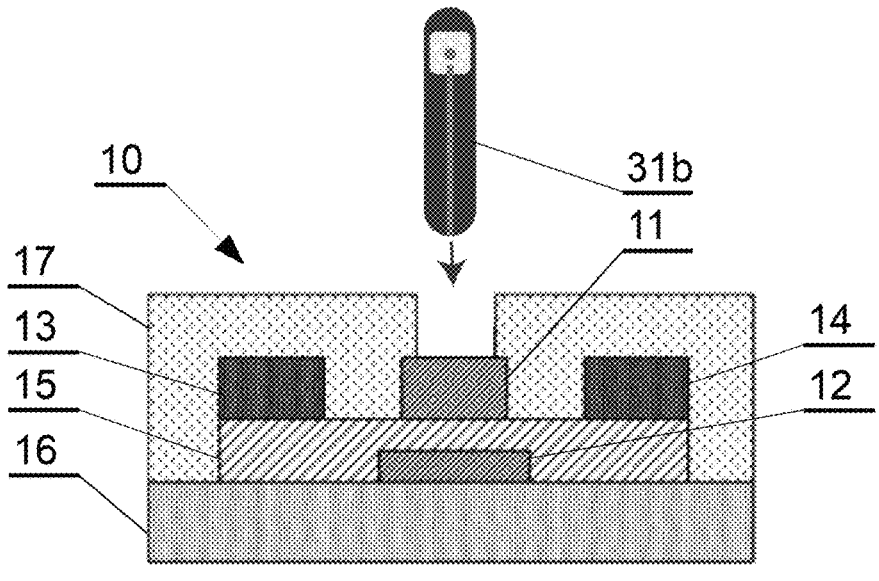
FIG. 1B: a cross-sectional view of a second embodiment of the detection transistor.

FIGS. 1A and 1B respectively depict a first and a second embodiment of a detection transistor 10, suitable for use in a biosensor according to the invention. The detection transistor 10 is a metal-semiconductor field-effect transistor (MESFET) that can be used as a component of the biosensor device for detecting one or more target substances during a single assay. The biosensor may be configured to detect target substances such as sugar (e.g., glucose), proteins, amino acid sequences (e.g., D/L-tryptophan (D/L-Trp), D/L-tyrosine (D/L-Tyr), and D/L-phenylalanine (L-Phe)), nucleotide sequences, etc. The biosensor is configured to detect whether the target substance is contained in a sample, such as saliva, blood, urine, sweat, or another biological fluid taken from a human or animal body.

The detection transistor 10 comprises a source electrode 13 and a drain electrode 14, connected by a semiconducting channel 15. During the assay, a drain-source current ($I_{DS}$) can flow through the channel 15, between the source and drain electrodes 13, 14. Additionally, the detection transistor 10 comprises a first gate electrode 11 positioned over the channel 15. The first gate electrode 11 is configured to be sensitive to the target substance during the assay. The detection transistor 10 further comprises a second gate electrode 12 configured to modulate the drain-source current of the channel 15 during the assay. This modulation provides compensation, at least to some extent, for the influence of interfering factors such as electrolytes and nitrogenous substances on the detection results. The second gate electrode 12 stabilizes the transistor's operating point by maintaining the channel's transconductance constant. The second gate electrode 12 is separated from the first gate electrode 11 by the channel 15 and is positioned on the channel's opposite side relative to the first gate electrode 11. For proper operation, both gate electrodes 11 and 12 should form Schottky junctions with the channel layer.

The second gate electrode 12 is positioned along the channel 15 in an area opposite the first gate electrode 11, but not adjacent to the source electrode 13 or the drain electrode 14. In other words, the second gate electrode 12 is located at the bottom side of the channel 15 between the source electrode 13 and the drain electrode 14, overlaps with the area of the first gate electrode 11, and has a width smaller than the distance between the source electrode 13 and the drain electrode 14.

The detection transistor 10 is arranged on an isolating substrate 16, so the second gate electrode 12 and the channel 15 are in contact with the isolating substrate 16 and physically separated from the remaining elements (11, 13, 14) of the detection transistor 10.

The source electrode 13, the drain electrode 14, and the first gate electrode 11 are arranged on the channel 15, with the first gate electrode 11 is arranged between the source electrode 13 and the drain electrode 14.

The source and drain electrodes 13, 14 can be made of various metals that can serve as ohmic contacts, such as molybdenum (Mo) or aluminum (Al). The first and second gate electrodes 11, 12 form Schottky contacts with the channel 15 and are preferably made of high work-function materials such as AgOx or PtOx, PdOx. The channel 15 is made of an oxide semiconductor such as In—Ga—Zn—O, In—Zn—O, ZnO, SnO$_2$, NiO. In—Ga—Zn—O (IGZO) is particularly preferred because it exhibits electron mobility above 10 cm$^2$ V-1 s-1, an amorphous microstructure, and ease of large area uniform thin film formation even at room temperature. It also provides stable, low operation voltages and high switching speeds of the detection transistor 10, all of which are desirable in biosensor applications.

The detection transistor 10 is preferably covered with an encapsulation 17, e.g. made of a polymer, such as SU-8 (i.e. an epoxy-based negative photoresist), PDMS (poly(dimethylsiloxane)), or PMMA (poly(methyl methacrylate)) to protect the transistor components from environmental conditions that could negatively affect the transistor's materials. The encapsulation 17 can prevent or at least restrict the penetration of moisture and oxygen into the transistor. The encapsulation 17 is arranged to expose the area of the first gate electrode 11 that is configured to be sensitive to the target substance, thus allowing the target substance to be captured by this area of the first gate electrode 11, if it is configured to be sensitive.

Figure 3A:
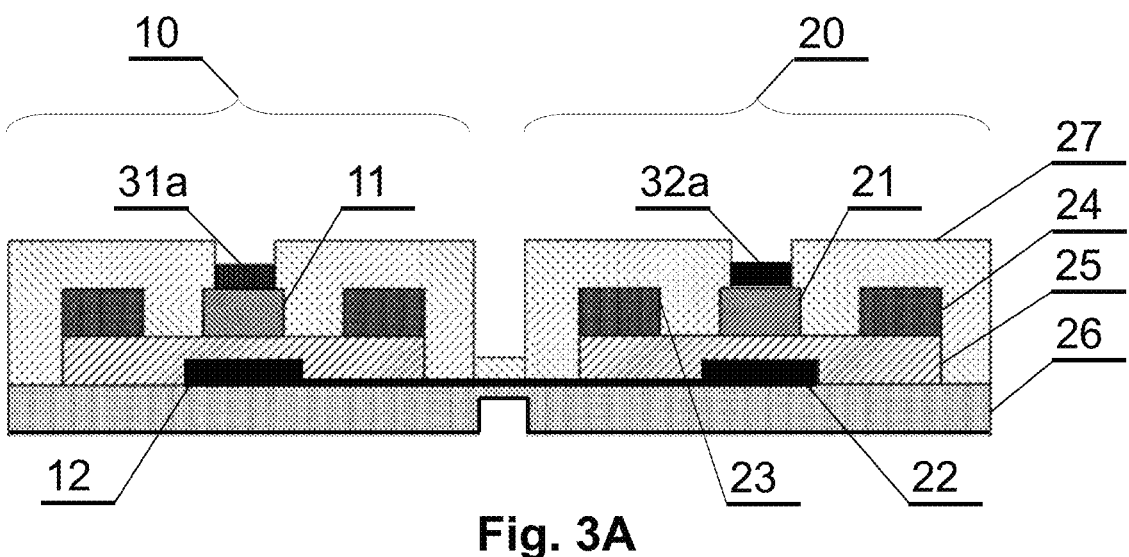
FIGS. 3A, 3B: a biosensing unit, which includes the detection transistor and a reference transistor, according to another embodiment of the present invention.
Figure 3B:
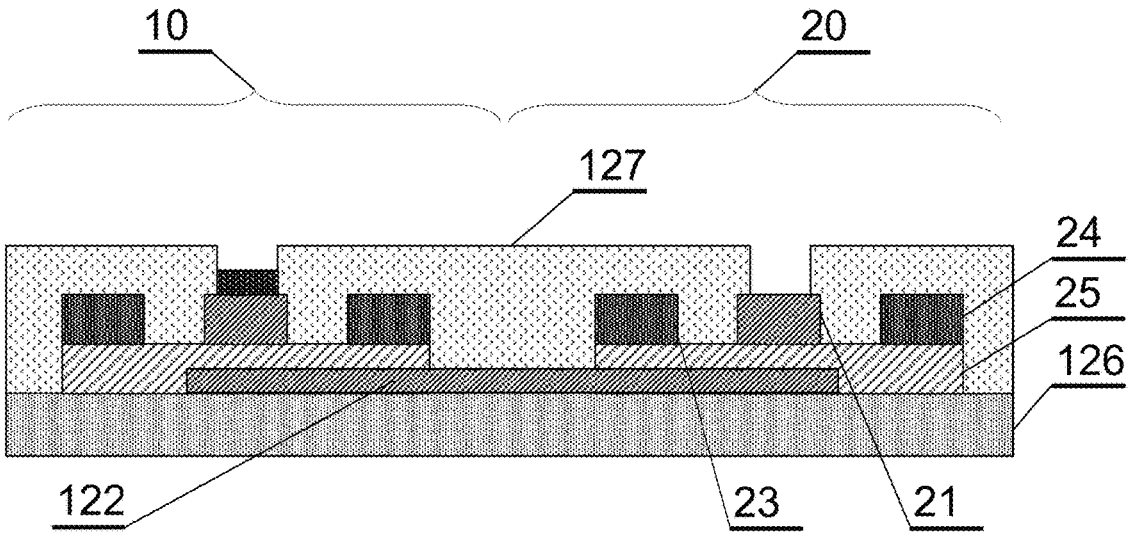
Figure 4:
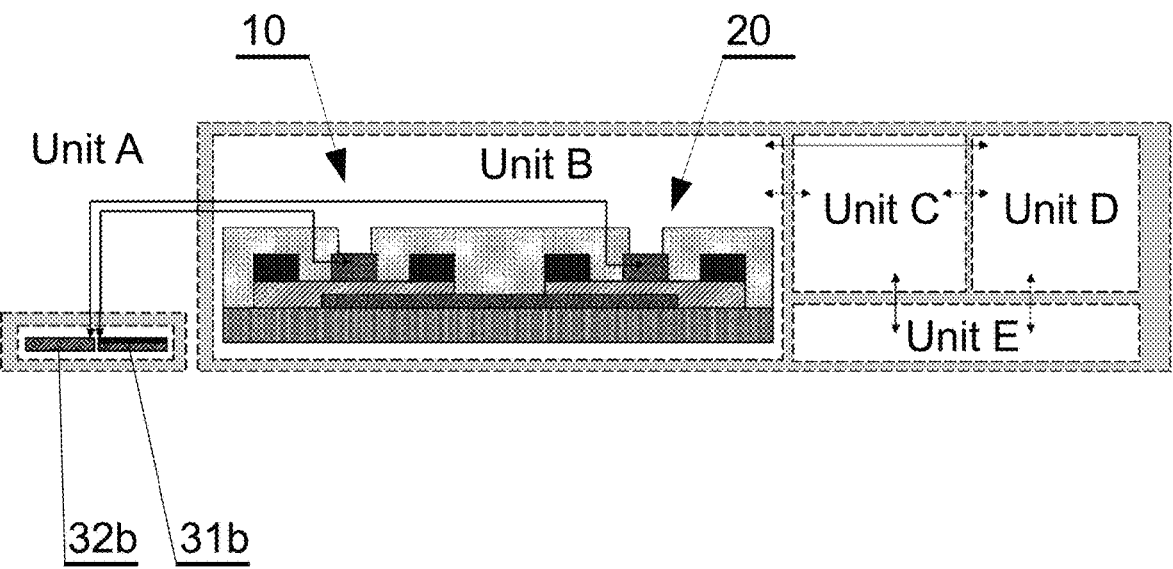
FIG. 4: a biosensor incorporating the biosensor unit.

The present invention further pertains to a biosensor device, such as shown in an embodiment in FIG. 4. The biosensor comprises a biosensing unit B, which may consist essentially of the detection transistor 10. Alternatively, the biosensing unit B may comprise the detection transistor 10 and a reference transistor 20 connected to each other, as shown schematically in FIGS. 3A and 3B.

In one specific embodiment, the biosensing unit B's reference transistor 20 may have the same design as the detection transistor 10. The reference transistor 20 comprises a source electrode 23 and a drain electrode 24, connected by a channel 25. This allows a drain-source current ($I_{DS}$) to flow through the channel 25 between the source and drain electrodes 23, 24 during the assay. Additionally, the reference transistor 20 incorporates a first gate electrode 21 positioned over the channel 25, which is configured to be insensitive to the target substance during the assay. The reference transistor 20 also includes a second gate electrode 22 designed to modulate the drain-source current of the channel 25, thereby stabilizing the operating point of the reference transistor. The second gate electrode 22 is physically separated from the first gate electrode 21 by a material of the channel 25. Preferably, the reference transistor is arranged on an isolating substrate 26, which can be made of SiO2 or another isolating material such as plastic foil, for example, PET foil. The source electrode 23, the drain electrode 24, and the first gate electrode 21 are arranged on the channel 25, with the first gate electrode 21 positioned between the source electrode 23 and the drain electrode 24. The source and drain electrodes 23, 24 can be made from various metals that can serve as ohmic contacts, such as molybdenum (Mo) or aluminum (Al). The first and second gate electrodes 21, 22 are Schottky contacts to the channel 25 and can be made from various materials such as AgOx or PtOx, PdOx, etc. The channel 25 is made of a semiconductor, preferably an oxide semiconductor such as In—Ga—Zn—O (IGZO), as this semiconductor exhibits electron mobility above 10 cm2 V-1 s-1, an amorphous microstructure, and ease of large area uniform thin film formation even at room temperature. It also provides stable, low operation voltages and high switching speeds for the reference transistor 20—all of these advantages are desirable in biosensor applications.

Furthermore, the detection transistor 10 and the reference transistor 20, arranged together in the biosensing unit B, may have the same proportions, geometry, architecture, dimensions, and they can be made of the same materials, except for the first gate electrode 21 of the reference transistor 20, which is configured to be insensitive to the target substance, particularly during the assay.

The biosensing unit B of the biosensor, comprising the detection transistor 10 and the reference transistor 20, is depicted in FIG. 4, and FIGS. 3A and 3B in isolation from the remaining units of the device. The device can further comprise a control unit C, a power supply unit D, and optionally a display unit E, to register and process signals from the biosensing unit B, and to visualize the obtained detection results. The respective units C, D, E may be made of known hardware, such as a microcontroller powered from a power source, as well as a display panel for data visualization, operable by suitable software for data processing.

As shown in FIG. 3A, within the biosensing unit B of the biosensor, the detection transistor 10 and the reference transistor 20 have their second gate electrodes 12, 22 electrically connected. This allows the second gate electrode 12 of the detection transistor 10 and the second gate electrode 22 of the reference transistor 20 to be maintained under the same bias, preferably under the same constant bias throughout the entire assay procedure. In one preferred embodiment of the biosensing unit B, shown in FIG. 3B, the second gate electrode of the detection transistor 10 and the second gate electrode of the reference transistor 20 are arranged as a common second gate electrode 122—formed by a coherent piece of material. The common second gate electrode 122 extends between the channels 15, 25 of both transistors 10, 20 so that the common second gate electrode 122 is physically separated by those channels 15, 25 from the first gate electrode 11 of the detection transistor 10 and the first gate electrode 21 of the reference transistor 20, respectively. The common second gate electrode 122 is positioned along the channel 15 in an area to which at the opposite side of the channel there are adjacent the first gate electrodes 11 and 21 and only one of the source or drain of the transistors 10, 20, but not both the source and drain of both transistors 10, 20. In other words, the common second gate electrode 122 is located at the bottom side of the channel 15 between the source electrode 13 of the detection transistor 10 and the drain electrode 24 of the reference transistor 20, overlaps with the area of the first gate electrodes 11, 21 and has a width that is smaller than the distance between the source electrode 13 of the detection transistor 10 and the drain electrode 24 of the reference transistor 20.

The transistors 10 and 20 may be arranged on the common substrate 126 and covered with a common encapsulation 127, exposing the first gate electrodes 11, 21 of both transistors, the detection transistor 10, and the reference transistor 20. Furthermore, the biosensing unit B may include multiple pairs of detection transistor-reference transistor, which can further increase the assay's sensitivity.

The first gate electrode 11 of the detection transistor 10 can be connected with a sensitive substrate 31a, 31b with functionalization species—suitable for interaction with the target substance. The functionalization species of the sensitive substrate 31a, 31b may be chemical molecules e.g. enzymes, antigens, nucleotide sequences e.g. DNA, or RNA, amino-acids sequences, or chemical groups, e.g. —COOH, —NH$_2$, —OH, which are capable of interaction with the target substance. For example, for the target substance being glucose, the sensitive substrate 31a, 31b may comprise glucose oxidase molecules serving as the functionalization species. The sensitive substrate 31a, 31b may also comprise a base material (inert to the target substance)—for suitable adherence of the functionalization species within the sensitive substrate 31a, 31b.

The first gate electrode 21 of the reference transistor 20 can be connected with an insensitive substrate 32a, 32b (FIGS. 3A, 4) without functionalization species, thus, the insensitive substrate 32a, 32b is unsuitable for interaction with the target substance. However, the insensitive substrate 32a, 32b is configured to detect at least one of the external factors which may impact the detection—distorting the results. For example, the insensitive substrate 32a, 32b may be configured to measure pH of the sample, thereby providing a reference that enables the minimization of interferents' influence on the measurement results. Preferably, the insensitive substrate 32a, 32b is made of the same base material connected to the electrode 21 as the base material of the sensitive substrate 31a, 31b-connected to the electrode 11 (however, the base material of the insensitive substrate 32a, 32b does not include the functionalization species).

The base material for both the sensitive and insensitive substrates, denoted as 31a, 31b, 32a, 32b, may be composed of a polymer, resin, or oligomer. For instance, the base material could be a conductive membrane polymer, such as Nafion®, which is directly attached to the first gate electrode, 11, 21. For the sensitive substrate, 31a, 31b, the membrane polymer may include enzymes, such as glucose oxidase for interaction with glucose.

The first gate electrode, 11, of the detection transistor, 10, can be connected with the sensitive substrate, 31a, and the first gate electrode, 21, of the reference transistor, 20, can be connected with the insensitive substrate, 32a, 32b. This connection can be achieved either by physical or chemical binding, ensuring that the substrate, 31a, 32a, once placed on the first gate electrode, 11, 21, is undetachable. Consequently, the biosensing unit B of the biosensor becomes disposable. This is depicted schematically in FIG. 1A for the detection transistor, 10, and in FIG. 3A for the biosensing unit B. Here, the sensitive substrate, 31a, and the insensitive substrate, 32a, are arranged as layers directly on the first gate electrode, 11, 21, respectively. The sensitive substrate, 31a, as well as the insensitive substrate, 32a, may be bonded to the first gate electrode, 11, 21, through chemical bonding, such as covalent bonds, ionic bonds, etc.

Figure 6A:
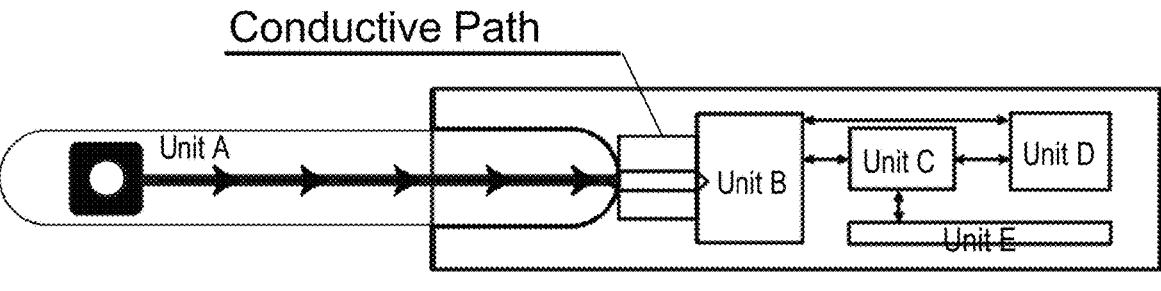
FIG. 6A: a schematic enlargement of the biosensing kit with a disposable substrate connected to the biosensing unit.

In another embodiment, the substrates, 31b, 32b, can be detachably connected to the respective first gate electrodes, 11, 21, via a conductive path (FIG. 6A). This allows for repeated connection and disconnection of the first gate electrode, 11, and the respective substrate (sensitive and insensitive, 31b, 32b), making the sensitive and insensitive substrate, 31b, 32b, disposable. The advantage of disposable substrates, 31b, 32b, is that the biosensing unit B of the biosensor, and thus, all the transistors can be used multiple times, allowing for multiple assays during the lifetime of the biosensing device. This can significantly reduce the cost of single assays and limit waste generation.

Figure 5:
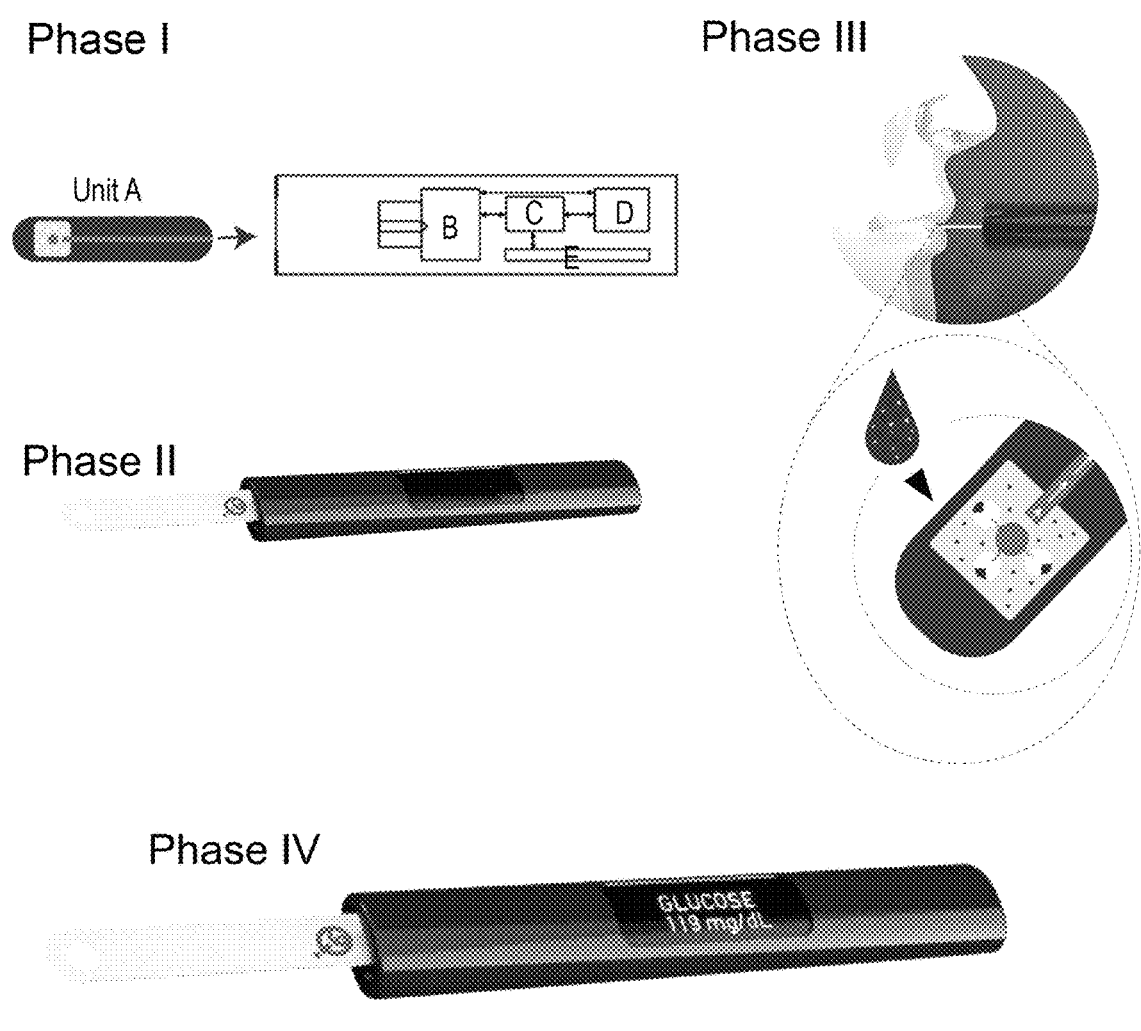
FIG. 5: a diagram illustrating the usage of a biosensing kit.

The conductive path, which makes both sensitive and insensitive substrates, 31b, 32b, disposable, can take various forms, including but not limited to conductive films, wiring, junction connectors, an electrolytic connection, etc. Furthermore, the detachable disposable substrates, 31b, 32b, may collectively form a single disposable strip (FIG. 5—Unit A). This strip comprises a sheet of material, for example, made of the base material, or comprising the base material with a sensitive zone arranged thereon with the functionalization species, and an insensitive zone without functionalization species. This allows both the sensitive substrate, 31b, and the insensitive substrate, 32b, to be simultaneously subjected to interaction with a single sample suspected to contain the target substance. This provides unified conditions of the assay for the entire biosensing unit B of the biosensor, as shown schematically in FIG. 4.

The assay for detecting the target substance with a biosensing kit, comprising the biosensor with the biosensing unit B, and the disposable unit A, comprising the sensitive substrate, 31b, and optionally further comprising the insensitive substrate, 32b, is shown schematically in FIG. 5. In phase one (I), the strip (unit A) with the sensitive substrate 31b and the biosensor are provided (for the example where the biosensing unit comprises only the detection transistor 10—the detachable strip comprises only the sensitive substrate 31b, and for the example where the biosensing unit further comprises the reference transistor 20—the detachable strip further comprises the insensitive substrate 32b, which are provided in two zones of the strip). In phase two (II), the user attaches the disposable strip to the biosensing unit using the conductive path. This ensures that the disposable strip is connected with the first gate electrode, 11, of the detection transistor, 10, and optionally with the first gate electrode, 21, of the reference transistor, 20, if present, as shown schematically in FIG. 6A. In phase three (III), the user brings the sample, suspected to contain the target substance, into contact with the detachable strip, both the sensitive and insensitive zones at once. For example, a saliva sample can be drawn directly from the mouth by holding the strip in the user's mouth for a specified period, typically from 1 to several seconds (as shown in FIG. 5—phase III). The units C-E of the biosensor conduct signal gathering and calculation, with the result being directly displayed on a screen of the biosensor, as shown in FIG. 5—phase four (IV). Additionally, the obtained data can be wirelessly transferred to an external device (such as a mobile phone, tablet, etc.) and processed externally by dedicated applications. The corresponding assays can be conducted for samples in various forms, e.g., blood, sweat, urine. The sample can be brought into contact with the sensitive substrate, $31b$, (and optionally with the insensitive substrate, $32b$, if provided in the disposable strip—unit A), prior to, during, or after connecting unit A with unit B of the biosensing kit, using the conductive path.

Detection Method

The assay is based on measuring the output characteristics: $I_{DS}$ (drain-source current) as a function of $V_{DS}$ (drain-source voltage) of the detection transistor, 10. The drain current ($I_{DS}$) changes as a function of the concentration of the target substance, which is attributed to changes in the electrical potential (modulation of the depletion region at the gate-channel Schottky region) on the first gate electrode, 11, 31*a*, 31*b*. This corresponds with the electrochemistry of interactions of the functionalization species of the sensitive substrate, 31*a*, 31*b*, and the target substance.

For instance, for glucose detection, the enzyme (glucose oxidase) can be contained in the sensitive substrate for selectively oxidizing glucose. Due to the oxidation reaction, gluconolactone and H2O2 particles are created as the reaction products, as described in Equation 1:

$$\text{Glucose} + O_2 \xrightarrow[\rightarrow]{\text{(glucose oxidase)}} \text{gluconolactone} + H_2O_2 \tag{1}$$

Next, the H2O2 dissociates into protons (H+), electrons (e−), and O2, as described in Equation 2:

$$H_2O_2 \rightarrow O_2 + 2H^+ + 2e^- \tag{2}$$

Figure 6B:
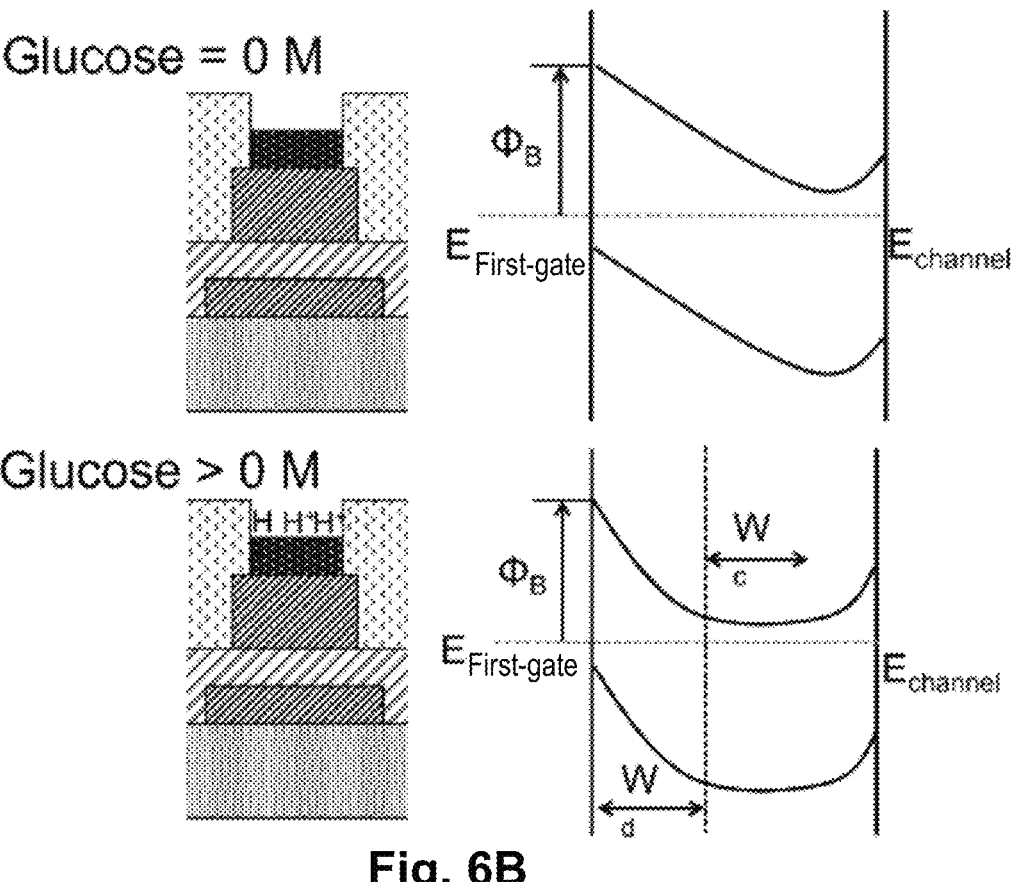
FIG. 6B: examples of energy band diagrams of a first gate electrode and channel of the detection transistor in pinch-off (0% glucose) and conducting (>0% glucose) states.

The net result of the above two reactions, according to Equations 1 and 2, is that a stoichiometric quantity of protons is liberated, which is directly proportional to the number of glucose molecules oxidized by the enzyme. The protons, being charged, affect a depletion region of the detection transistor, and therefore affect the drain-source current ($I_{DS}$) (FIG. 6B). As presented in FIG. 6B, at 0% of the target substance (e.g., glucose) in the sample subjected to assay, the channel is nearly pinched off and the current flowing through the channel is low. As the target substance (e.g., glucose) concentration increases, the depletion region thickness (Wd) decreases, subsequently increasing the width of the conduction channel (Wc). This leads to a decrease in the barrier potential and the resistivity between the source electrode and the drain electrode in the channel, which is followed by an increase in the drain-source current ($I_{DS}$).

Figure 2A:
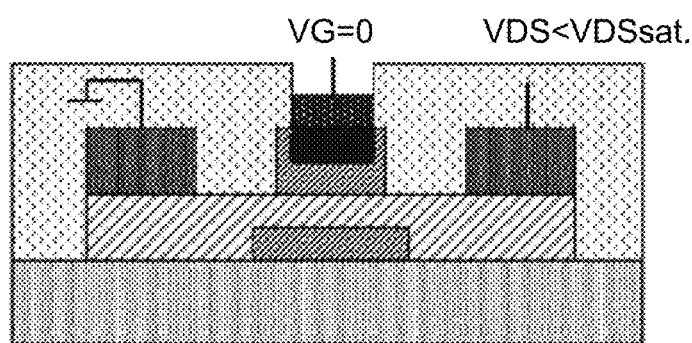
FIGS. 2A-2C: a general principle of operation of the detection transistor.
Figure 2B:
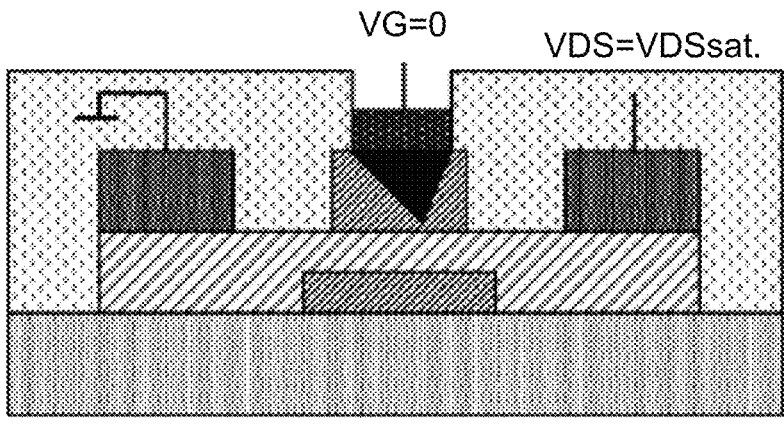
Figure 2C:
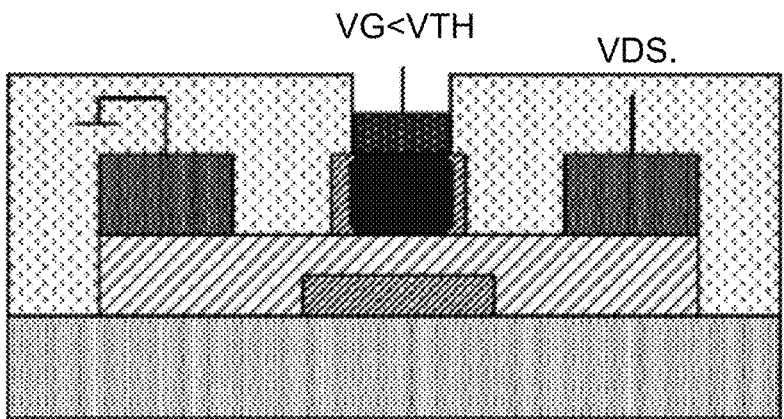

FIGS. 2A-2C graphically illustrate the electrical measurements that can be taken during the assay with a biosensor. This biosensor includes a biosensing unit B, which features a detection transistor 10. As previously mentioned, the detection transistor measures the target substance by assessing output characteristics: $I_{DS}$=f ($V_{DS}$) of the biosensor. The detection transistor (MESFET) has two gate electrodes: the first gate electrode and the second gate electrode. It also includes a channel between the electrodes that operates under a constant bias of the second gate electrode.

In the absence of polarization of the second gate electrode, the initial gate-source voltage (VGS) is 0, and the drain-source voltage ($V_{DS}$) is also 0. Under these conditions, the detection transistor is in thermodynamic equilibrium and no current flows. A depletion layer exists beneath the first-gate Schottky junction. By increasing $V_{DS}$>0 V, the source-drain current ($I_{DS}$) will flow due to the potential difference between the source electrode and the drain electrode, as shown in FIG. 2A. Initially, for low $V_{DS}$, the channel resistance remains constant, and $I_{DS}$ is linearly dependent on $V_{DS}$ according to Ohm's law. As $V_{DS}$ increases, the Schottky barrier becomes increasingly reverse biased, causing the voltage to drop across the channel. This potential difference results in an expansion of the depletion layer at the drain electrode side of the channel Consequently, the channel narrows at the drain electrode side, leading to the rounding off of the source-drain current ($I_{DS}$). At a specific voltage, known as the saturation drain-source voltage ($V_{DSsat}$), the width of the depletion layer equals the channel thickness, resulting in the channel being pinched off, as depicted in FIG. 2B. At this drain-source voltage ($V_{DS}$), the source electrode and the drain electrode are completely separated by a reverse-biased depletion region. Despite the pinch-off and the resulting lack of charges, the source-drain current ($I_{DS}$) continues to flow due to the injection of carriers through the depletion layer at the high electric field in this region. A further increase in $V_{DS}$ shifts the pinch-off point towards the source contact, and further increases in $V_{DS}$ saturate the diffusive source-drain current ($I_{DSsat}$) Excessive increases in $V_{DS}$ can lead to the breakdown of the channel. The charge-depleted region in the channel can also be controlled by varying the first-gate-source voltage (VGS). As VGS becomes more negative, the depletion width increases due to the drain-first gate junction becoming more reverse biased, as shown in FIG. 2C. The variation in VGS aligns with changes in the concentration of the monitored target substance, such as biochemical species. This, in turn, causes the channel region to pinch off at lower drain voltages.

The design of the detection transistor 10 and the reference transistor 20, according to the present invention, includes the first gate electrode and the second gate electrode. The second gate electrode 12, 22, 122, as previously mentioned, is polarized to set the operating point of the device. The first gate electrode of the detection transistor 10 is sensitive to the target substance (when combined with the substrate 31*a*, 31*b*). The interaction of the target substance with the functionalization species of the substrate directly influences the channel conductance of the detection transistor, as a function of the monitored target substance. Furthermore, the second gate electrode of the detection transistor is used to control and reduce the feedback capacitance between the input and output, thereby setting the operating point of the device and enhancing the stability of both the measurement and the MESFET. The detection transistor 10 with the second gate electrode 12 demonstrates higher thermal stability during detection, providing compensation for external interfering factors such as temperature.

Additionally, the biosensor, which includes the detection transistor 10 and the reference transistor 20, offers improved compensation for external factors, such as the pH of the sample, which can vary among users. The reference transistor, in combination with the detection transistor, can function as a pH meter, correcting the signal obtained from the detection transistor with the signal obtained from the reference transistor. The depletion region in the channel of the reference transistor is influenced by the total charge of the analyte (i.e., the sample), while the detection transistor operates as described above. Specifically, the depletion region in the channel of the detection transistor corresponds to the pH affected by the redox reaction between the functionalization species and the monitored target substance. The difference between the signal of the detection transistor and the signal of the reference transistor provides a deconvoluted signal that is highly correlated only with the target substance, for example, glucose. By pairing detection and reference transistors, the accuracy of the measurement can be further improved. To this end, the difference between the value of integrated signals from all the detection transistors and the value of integrated signals from all the reference transistors is calculated. For one pair of detection-reference transistors, the final deconvoluted signal can be calculated according to Equation 3:

$$signal = \left( \int (I_{DS_{TFT10}}) - \int (I_{DS_{TFT20}}) \right) dI_{DS} \qquad (3)$$

wherein:

signal—denotes the signal obtained as the result of the measurement, $I_{DS_{TFT10}}$—denotes drain-source current of the detection transistor, $I_{DS_{TFT20}}$—denotes drain-source current of the reference transistor.

For more than one pair, e.g., n pairs of detection-reference transistors (each pair comprising one detection transistor and one reference transistor connected as shown in FIG. 3A or 3B), the final deconvoluted signal can be calculated according to Equation 4:

$$signal = n\left( \int (I_{DS_{TFT10}}) - \int (I_{DS_{TFT20}}) \right) dI_{DS} \qquad (4)$$

Figure 7:
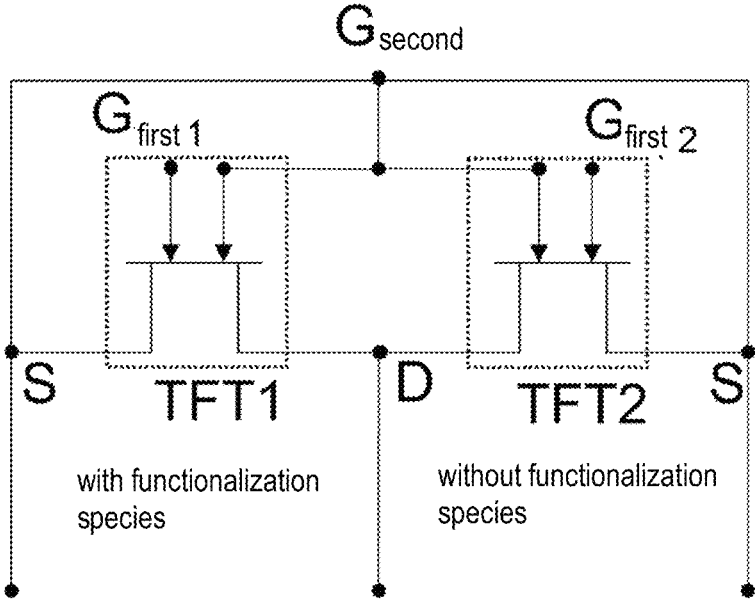
FIG. 7: an electrical schematic of the biosensor unit, comprising the detection transistor and the reference transistor, according to the present invention.

FIG. 7 presents the electrical scheme of the two transistors, the detection transistor with the first gate electrode sensitive to the target substance and the reference transistor with the first gate electrode insensitive to the target substance. The transistors are connected by a common second gate electrode 122, which is maintained under constant bias. In other words, the second gate electrodes of both transistors are at the same potential. Similarly, equal voltage is set between the source electrode and the drain electrode of both transistors. The first gate electrodes of both transistors are nonpolarized (floating) and both have direct contact with the target substance during detection. The second gate electrode is connected to the control system (such as a microprocessor) in the unit C of the biosensor (shown in FIG. 4). This connection stabilizes the operating point and tailors the transfer characteristic, further stabilizing the operating point.

The respective signals received from the detection transistor and the reference transistor are calculated for their difference, utilizing a microprocessor equipped with software for standard signal processing tasks such as sampling and smoothing. This data can be wirelessly transferred to an external device, such as a mobile device, for further processing. The potential of the common second gate electrode is set in accordance with the program at the microcontroller unit. The final result of the completed assay may be obtained by probing and integrating the drain-source current from both the detection transistor and the reference transistor in the time domain, and processing (subtracting) in the external application to deconvolute a value corresponding solely to the concentration of the target substance (e.g., glucose). The resulting value of the source-drain current is proportional to the concentration of the target substance being detected.

The biosensor and the biosensing kit according to the present invention, offer flexibility in detecting various biochemicals. The functionalization species contained in the substrate 31*a*, 31*b*, can be a glucose oxidase or another biomaterial such as a different enzyme, antibody, DNA, a receptor, or another type of capturing molecule biologically specific for the target substance. When the target substance is present in the sample, it interacts with the functionalization species, modulating the conductivity of the channel of the detection transistor and thereby the drain current. Changes proportional to the volume of analyzed biochemicals can be directly read by Unit C of the biosensor and visualized on the display as well as wirelessly transferred to a mobile device, such as a smartphone, providing rapid and reliable assay results. Therefore, the assay with the biosensing kit according to the present invention can be performed directly by the user under domestic conditions, without the need for professional healthcare workers.

Example 1—A Method for Preparing the Substrate for Glucose Detection Directly on the First Gate Electrode of the Transistor A glucose oxidase functionalizing solution was prepared by dissolving 15 mg of enzyme powder (glucose oxidase) in 0.15 M phosphate-buffered saline. The obtained glucose oxidase functionalizing solution was mixed with a polymeric membrane made of Nafion® (C7HF13O5S·C2F4) in a 1:1 volume ratio and stirred for 50 minutes to form a clear solution. This clear solution was drop cast (although it could alternatively be inkjet printed) onto the first gate electrode of the MESFET transformer and then dried at 6° C. for 12 hours. The resulting transistor was designed according to FIG. 1A.

Example 2—an Example of Operation

Figure 8:
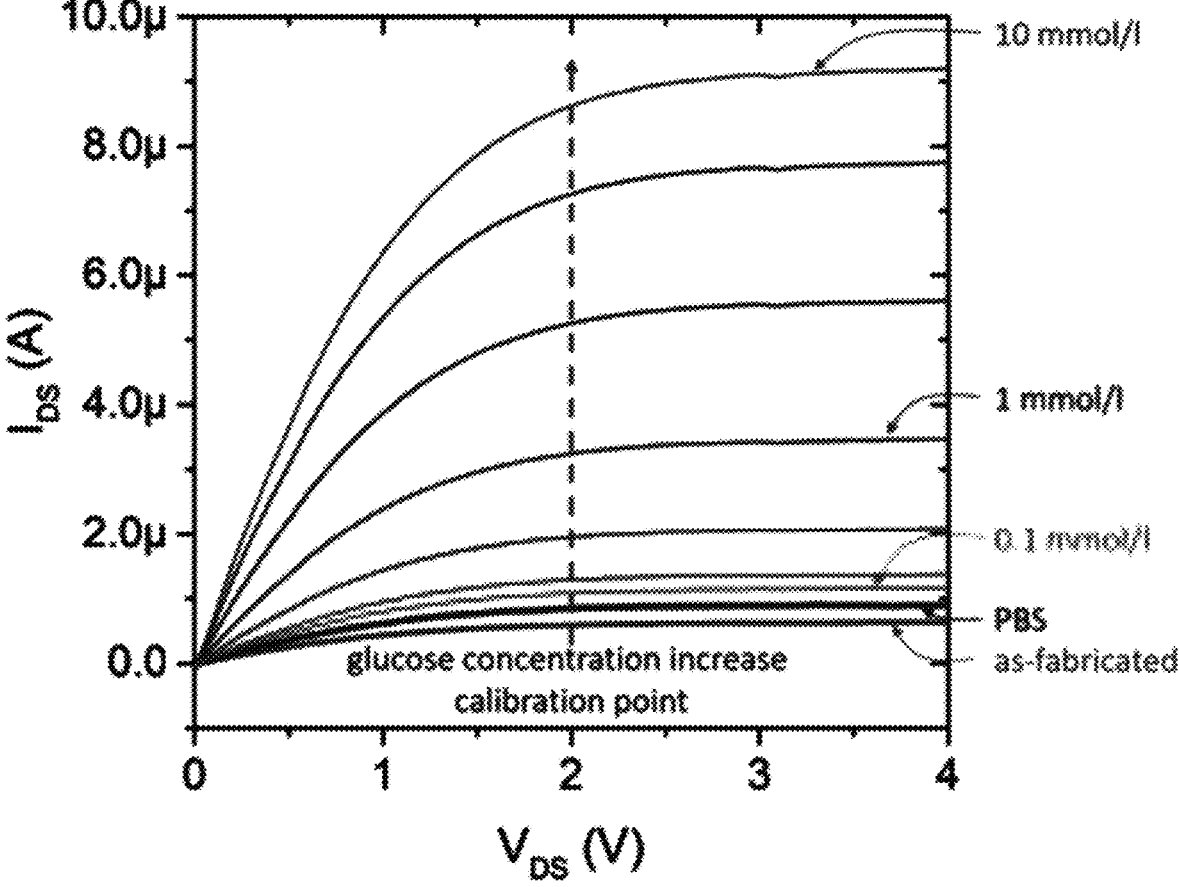
FIG. 8: output characteristics of the detection transistor.

Glucose detection was performed by measuring the output characteristics of both the detection and reference transistors. The output characteristics of the detection transistor are depicted in FIG. 8.

At 0% glucose concentration in the analyte, the channel is nearly pinched off and a current of 0.6 µA flows through the channel under $V_{DS}$=2 V. As the glucose concentration increases, the depletion region thickness decreases, subsequently increasing the width of the conduction channel. This leads to a decrease in resistivity between the source and drain in the channel, followed by an increase in the drain current, reaching 8.0 µA for a glucose concentration of 10 mmol*l-1 under $V_{DS}$=2 V. The final reading of the biosensor relies on subtracting these values from the signal coming from the unfunctionalized reference transistor, which corresponds to the plain value of pH.

The invention claimed is:

1. A biosensor comprising a detection transistor and a reference transistor, both of a metal-semiconductor field-effect (MESFET) type, for detecting a target substance, wherein:

the detection transistor comprises:

an isolating substrate,

13 a source electrode, a drain electrode, a first gate electrode, a channel for transmitting a drain-source current between the source electrode and the drain electrode, the channel being made of an oxide semiconductor, arranged on the isolating substrate and having the source electrode and the drain electrode arranged thereon, a sensitive substrate connected to the first gate electrode and comprising functionalization species for bonding the target substance, such that the first gate electrode connected with said substrate is sensitive to the target substance, and a second gate electrode arranged on the isolating substrate, physically separated from the first gate electrode by the channel, positioned opposite to the first gate electrode and configured to modulate the drain-source current of the channel;

and wherein the reference transistor comprises:

a reference source electrode, a reference drain electrode, a first reference gate electrode connected with an insensitive substrate without the functionalization species of the sensitive substrate, such that the first reference gate electrode connected with said insensitive substrate is insensitive to the target substance, a reference channel made of the oxide semiconductor, for transmitting a reference drain-source current between the reference source electrode and the reference drain electrode, and a second reference gate electrode physically separated from the first reference gate electrode by the reference channel, wherein the detection transistor and the reference transistor are both placed on the isolating substrate and electrically connected to one another, wherein the second gate electrode of the detection transistor is connected to the second reference gate electrode of the reference transistor.

2. The biosensor according to claim 1, wherein the second gate electrode is positioned along the channel in an area to which at the opposite side of the channel there is adjacent the first gate electrode and only one of the source electrode or the drain electrode.

3. The biosensor according to claim 1, further comprising an encapsulation arranged such that it exposes the first gate electrode.

4. The biosensor according to claim 1, wherein the first gate electrode is connected with the sensitive substrate via a deposition of the substrate on the first gate electrode.

5. The biosensor according to claim 1, wherein the first gate electrode is connected with the sensitive substrate via a conductive path.

6. The biosensor according to claim 5, wherein the conductive path is selected from the group consisting of conductive film, wiring, junction connector, and electrolytic connection.

7. The biosensor according to claim 6, wherein the sensitive substrate is arranged on a disposable strip comprising a sheet of material with the functionalization species, for detachably connecting with the first gate electrode.

8. The biosensor according to claim 1, wherein the isolating substrate is elastic.

9. The biosensor according to claim 1, wherein the second gate electrode of the detection transistor and the second reference gate electrode of the reference transistor are arranged as a common second gate electrode of both transistors, formed from a coherent piece of material.

10. The biosensor according to claim 9, wherein the common second gate electrode extends from the channel of the detection transistor to the reference channel of the reference transistor, wherein said channels separate the common second gate electrode from the first gate electrodes of the detection transistor and from the first reference gate electrode of the reference transistor.

11. The biosensor according to claim 1, wherein the detection transistor and the reference transistor are covered with a common encapsulation.

12. A biosensing device comprising the biosensor according to claim 1 and further comprising:

a control unit for processing measured data;

a power supply unit for powering the device; and a data display unit for visualizing a detection result.

13. A biosensing kit comprising:

the biosensor according to claim 1, and a disposable substrate unit comprising:

the sensitive substrate with functionalization species sensitive to the target substance, detachably connectable with the first gate electrode of the detection transistor.

14. A biosensing kit comprising:

the biosensor according to claim 1, and:

a disposable substrate unit comprising:

the sensitive substrate with functionalization species sensitive to the target substance, detachably connectable with the first gate electrode of the detection transistor, and the insensitive substrate without functionalization species sensitive to the target substance, detachably connectable with the first reference gate electrode of the reference transistor.

* * * * *